United States Patent [19]

Munch

[11] Patent Number: 4,466,114
[45] Date of Patent: Aug. 14, 1984

[54] DEVICE FOR ROTATING AN ANTI-DIFFUSING SCREEN IN A RONTGEN TOMOGRAPH

[75] Inventor: Joseph Munch, Paris, France

[73] Assignee: Thomson-CSF, Paris, France

[21] Appl. No.: 385,291

[22] Filed: Jun. 4, 1982

[30] Foreign Application Priority Data

Jun. 10, 1981 [BE] Belgium .................................. 889159

[51] Int. Cl.³ ............................................ H01J 35/16
[52] U.S. Cl. .................................................. 378/155
[58] Field of Search ................................ 378/154, 155

[56] References Cited

U.S. PATENT DOCUMENTS 1,542,204  6/1925  Akerlund ............................ 378/155

Primary Examiner—Craig E. Church
Attorney, Agent, or Firm—Roland Plottel

[57] ABSTRACT

The device comprises essentially a base plate with annular guide groove, an endless annular control element freely placed and movable in said guide groove, connecting means placed between said annular control element and said anti-diffusing screen disposed at the center and a drive means for driving said annular control element and said anti-diffusing screen coupled thereto.

6 Claims, 3 Drawing Figures

U.S. Patent     Aug. 14, 1984     4,466,114
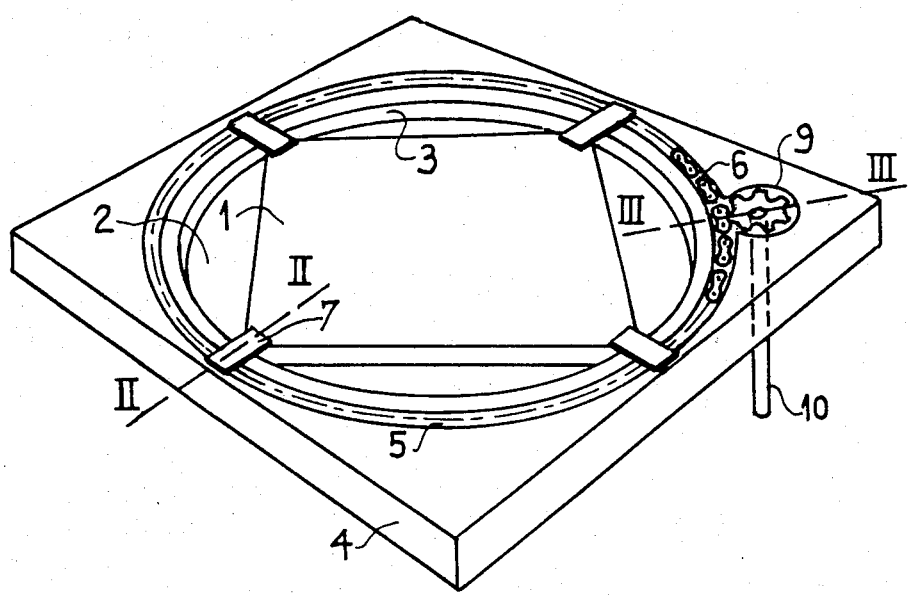
FIG_1
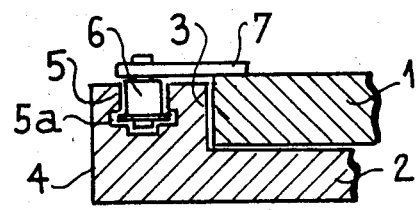
FIG_2
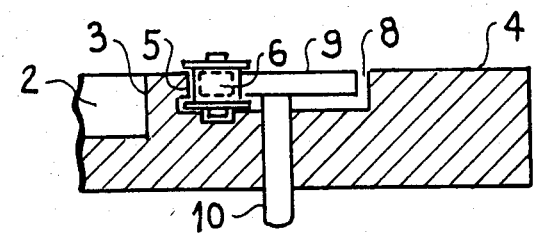
FIG_3

DEVICE FOR ROTATING AN ANTI-DIFFUSING SCREEN IN A RONTGEN TOMOGRAPH

BACKGROUND OF THE INVENTION

The invention relates to a device for rotating, at the periphery thereof and in a horizontal plane, an anti-diffusing screen without central shaft.

It is well known that the control of the rotational movement of such an anti-diffusing screen is required for directing the vertical slides, disposed close to one another, so that in the longitudinal direction, they run always in the direction of the Röntgen tube which moves circularly above the screen.

To arrive at this result, a device is known in which the anti-diffusing screen is mounted in a relatively large supporting disk or ring which, at its periphery, is provided with a chain or toothed belt in which a chain wheel or a toothed belt disk, which is driven in rotation, is engaged so as to rotate the anti-diffusing screen. The disk is then guided at its periphery by small guide wheels.

This device has however the disadvantage that the cost price thereof is relatively high and that mounting thereof is relatively complicated.

SUMMARY OF THE INVENTION

To obviate these disadvantages, the device of the invention comprises essentially a base plate with annular guide groove, an endless annular control element freely placed and movable in the above-mentioned guide groove, connecting means placed between the annular control element and the anti-diffusing screen disposed in the center, and drive means for driving the annular control element and the anti-diffusing frame coupled thereto.

This device has the advantage of being formed from few elements. In addition, its cost price is low.

BRIEF DESCRIPTION OF THE DRAWINGS

There is described herebelow by way of example one embodiment of said device in accordance with the invention, namely one possible embodiment thereof but in no wise limited to the embodiment described hereafter. The present description is accompanied by drawings in which:

FIG. 1 is a perspective view of the device;
FIG. 2 is a cross-section along line II—II of FIG. 1; and
FIG. 3 is a cross-section along line III—III of FIG. 1.

DESCRIPTION OF THE PREFERRED EMBODIMENT

In these figures it can be seen that the square frame of the anti-diffusing screen 1 is located in a circular hollow 2, provided with a vertical wall 3, in a base plate 4 made from a synthetic plastic material whose friction coefficient is very low. The dimensions of the circular hollow 2 and of the frame of the anti-diffusing screen 1 are chosen so that the anti-diffusing screen is sunk in the circular hollow 2 and so that it may be driven in this hollow. Around the circular hollow 2 there is provided, in base plate 4, an annular groove 5 whose cross-section has the shape of an inverted T. In this annular groove there is provided, with slight play, an endless articulated chain 6 connected by a connecting link 7 at four places to each angle of the frame of the anti-diffusing screen 1. In the base plate and right against the annular groove 5 there is provided a circular recess 8 which, laterally, leads into the abovementioned annular groove 5 in which is housed a chain wheel 9 which is engaged with the articulated chain 6 placed in the annular groove 5 and which is mounted on a control shaft 10. For mounting the device, the articulated chain 6 is fitted into the annular groove 5, through recess 8, so that the lower links of the articulated chain 6 are in the widened part 5a of the annular groove 5. Thus, the articulated chain 6, after being engaged with the chain wheel 9, may no longer come out of the annular groove 5 when the chain wheel 9 rotates it in a circle in the annular groove 5. During this movement, the connecting links 7 drag the anti-diffusing screen 1 in a circle within the circular hollow 2.

By using this means and choosing for the base plate 4 a suitable synthetic plastic material, the friction coefficient can be held within admissible limits, between the elements of the device.

It goes without saying that the shape and dimensions of the above-described elements, as well as the mounting thereof in their respective positions and the choice of the material to be used for manufacturing them may differ, provided that they remain within the scope of the invention.

What is claimed is:

1. A device for rotating an anti-diffusion screen in a Röntgen tomograph, comprising essentially a base plate with annular guide groove, an endless annular control element placed freely movable in said guide groove, connecting means placed between the annular control element and the anti-diffusing screen placed at the center and a drive means for driving the annular control element and the anti-diffusing screen coupled thereto.

2. The device as claimed in claim 1, wherein said annular guide groove has a cross-section in the shape of an inverted T, in which there is placed an endless articulated chain whose underlying links run in the widened part of said annular guide groove to maintain said articulated chain in said guide groove.

3. The device as claimed in claim 1, wherein said base plate is made from synthetic plastic material.

4. The device as claimed in claim 1, wherein said base plate is provided with a circular hollow in which is sunk said anti-diffusing screen.

5. The device as claimed in claim 2, wherein, in said base plate, there is provided a circular shaped recess which laterally leads into said annular guide groove for introducing said articulated chain into said guide groove and housing a chain wheel engaged with said articulated chain.

6. The device as claimed in claim 2, wherein said anti-diffusing screen is connected, at several places, and at its periphery to said articulated chain by connecting links.

* * * * *